United States Patent [19]

Pedersen et al.

[11] Patent Number: 4,523,464
[45] Date of Patent: Jun. 18, 1985

[54] FLOWMETER WITH NO MOVING PARTS

[75] Inventors: David R. Pedersen; Curtis M. Tong, both of Antioch, Calif.

[73] Assignee: The Dow Chemical Company, MidlandMI

[21] Appl. No.: 541,499

[22] Filed: Oct. 13, 1983

[51] Int. Cl.³ .............................................. G01F 1/20
[52] U.S. Cl. ..................................................... 73/216
[58] Field of Search ......................... 73/215, 216, 861

[56] References Cited

U.S. PATENT DOCUMENTS

| 187,623 | 2/1877 | Hambleton | 73/216 |
|---|---|---|---|
| 2,035,371 | 3/1936 | Johnson et al. | 73/216 |
| 3,001,397 | 9/1961 | Leonard | 73/861 |
| 3,340,871 | 9/1967 | Jellies | 73/215 X |
| 4,136,692 | 1/1979 | Goldowsity | 73/215 X |
| 4,203,820 | 5/1980 | Wiseman | 204/263 |
| 4,213,336 | 7/1980 | Schweickart et al. | 73/215 |
| 4,291,693 | 9/1981 | Todd | 73/215 X |
| 4,346,596 | 8/1982 | Diamant et al. | 73/215 X |
| 4,388,835 | 6/1983 | Rosaen | 73/861.58 |
| 4,395,918 | 8/1983 | Wilson | 73/861 |

OTHER PUBLICATIONS

D. M. Considine et al., *Handbook of Applied Instrumentation*, pp. 5-57 to 5-59, McGraw-Hill (1964).
*Kirk-Othmer, Encyclopedia of Chemical Technology*, 2nd Ed., pp. 473-475 (1966).

Primary Examiner—Herbert Goldstein
Attorney, Agent, or Firm—Michael L. Glenn

[57] ABSTRACT

A simple device for measuring flow rate of liquid in a partially-full pipe. This device comprises a generally vertical, first chamber into which liquid is introduced, a non-opaque, second generally vertical chamber in communication with the lower portion of the first chamber, an orifice communicating with the lower portion of the first and second chambers, an overflow leg and an outlet for liquid passing through the orifice or overflow. The height of liquid in the second chamber provides a visible indication of the flow rate.

9 Claims, 3 Drawing Figures

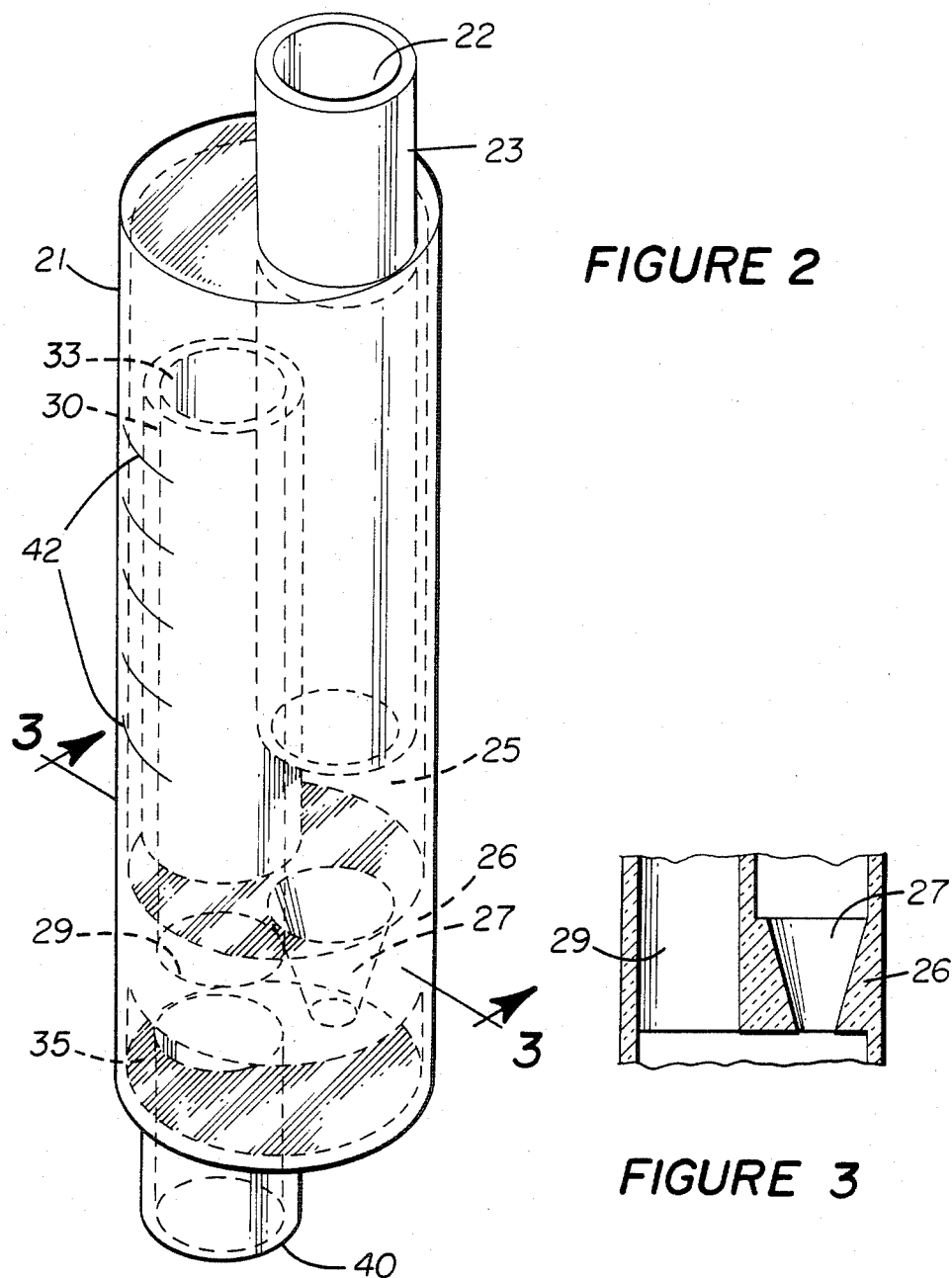

4,523,464

FLOWMETER WITH NO MOVING PARTS

BACKGROUND OF THE INVENTION

This invention relates to a device for measuring the flow of liquids. More specifically, this device provides a visual indication of liquid flow rate.

A variety of flowmeters are known in the prior art. These flowmeters fall into several fundamental categories. There are devices which use constricted orifices and determine flow from the measurement of pressure drop through the orifice. Some devices determine liquid flow rate via sound velocity measurement. Certain weir-type devices determine flow rate from the depth of liquid flowing over a crest or sill. Other devices use rotameter-type floating bobs to indicate flow rates. A variety of devices are cataloged in *Kirk-Othmer Encyclopedia of Chemical Technology*, 2nd Ed., Vol. 9, pp. 473–477 (1966).

In many applications it would be desirable to employ a simple, inexpensive flow measurement device. It would also be advantageous for this device to measure flow of liquids having low linear velocities in a partially full pipe or conduit.

SUMMARY OF THE INVENTION

The subject invention is a device which provides a visual indication of the flow rate of a liquid. This device comprises a housing containing a first and second chamber, a constricted orifice, connections between the first and second chamber and inlets and outlets. A liquid inlet into the housing communicates with the upper portion of the first, generally vertically-disposed chamber. The first chamber in its lower portion communicates with a constricted orifice. The orifice on the side opposite that in communication with the first chamber communicates with a liquid outlet. The first chamber also communicates with a second chamber in a region above the orifice. The orifice and first and second chambers are sized and disposed so that the height of liquid in the second chamber is proportional to the rate of flow of liquid introduced to the inlet. The second chamber has at least one generally vertical section of an externally visible wall extending below the point at which the liquid inlet communicates with the first chamber but above the orifice. This vertical section constitutes a flow measurement zone that indicates flow rate of liquid entering the device based on the height of liquid in the chamber. Means for determining the height of liquid in the second chamber and means for relating the height of liquid in the second chamber to the liquid flow rate must be provided. The second chamber also communicates with a liquid outlet in a region above the flow measurement zone.

DESCRIPTION OF THE DRAWINGS

FIG. 2 is a perspective view of another embodiment of the invention with internal details indicated by broken lines and shading.

FIG. 3 is a cross-sectional view of a portion of the invention depicted in FIG. 2.

DETAILED DESCRIPTION OF THE INVENTION

Figure 1:
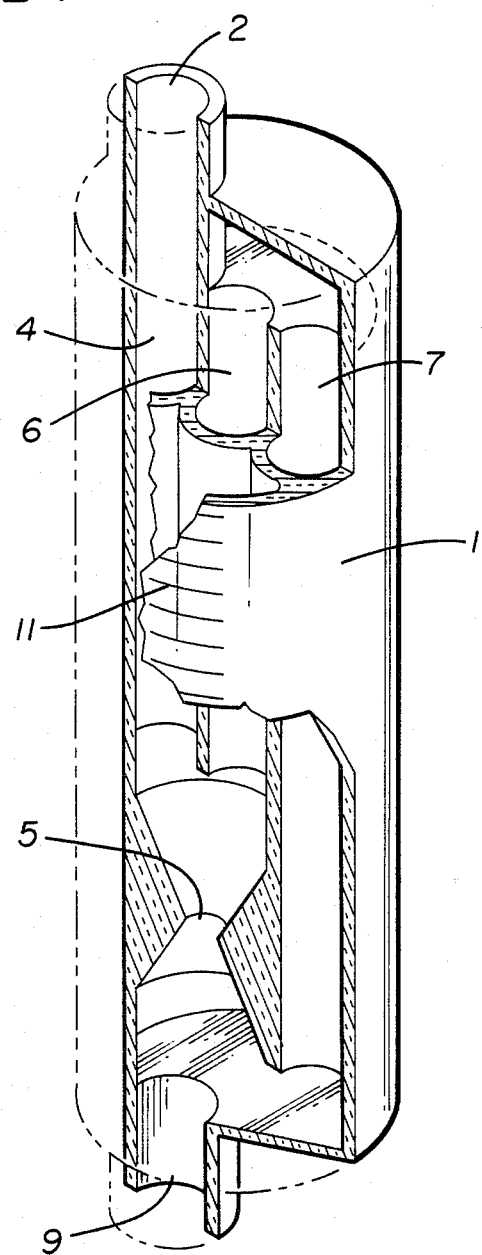
FIG. 1 is a cross-sectional view of one embodiment of the invention except for a small region that offers a perspective view.

The subject invention is a simple device which provides a visual indication of liquid flow. It can be easily fabricated from readily available thermoplastics or other inexpensive materials. Because it need not contain moving parts or complex electronics, this flow measurement device is exceptionally durable and reliable even in harsh operating environments.

The housing for the subject device can consist of nothing more than the walls of the first and/or second chambers joined by the appropriate connections and including the necessary inlets and outlets. Advantageously, in one preferred embodiment of the invention the portion of the housing in the flow measurement zone is sufficiently translucent or transparent so that the height of the liquid column can be determined by visual inspection. Conveniently, the entire piece containing the flow measurement zone is fabricated from a single transparent material, if the liquid column height is to be determined by visual inspection.

Various electronic or optical means known in the prior art can also be used to monitor and record the liquid column height. For example, the change in light transmittance in the second chamber when liquid is present affords a basis for monitoring liquid column height using a light source and photomultiplier. Radiation absorption by the liquid or the pressure the weight of the liquid exerts at the base of the column can also be used to determine height of the liquid. This flow rate information can in turn be used to adjust valves or gates if desired to maintain a desired flow rate.

Polycarbonate, poly(methyl methacrylate) and polysulfone are preferred materials of construction because of their strength, durability and transparency. The selection of appropriate construction materials must take into account the nature of the liquids which will contact the device and the means to be used to measure the liquid column height.

The operation of the subject flow measurement devices can be better understood by reference to the embodiments depicted in the drawings. In FIG. 1, the housing 1 contains a liquid inlet 2. Liquid introduced into the inlet 2 passes downwardly into the first chamber 4. Liquid passes from the first chamber 4 to the second chamber 6 seeking a level proportional to the liquid flow rate. Liquid passes from the two chambers 4 and 6 downwardly through the orifice 5 and then out the outlet 9. The first and second chambers 4 and 6 and the orifice 5 are sized so that at the average expected flow rate the height of the liquid column in chamber 6 falls approximately in the middle of the flow measurement zone indicated by flow calibration marks 11 visible on the housing 1. At slower than average flow rates the height of the liquid column in chamber 6 declines to a height proportional to the flow rate. Faster than average flow rates produces a corresponding increase in the height of liquid in the column in chamber 6. If the liquid flow rate exceeds designed capacity of the device, liquid flows from chamber 6 to overflow leg 7 and then to outlet 9. The overflow leg 7 also maintains equal gas pressures above and below the liquid in chamber 6 during normal operation. If the gas pressure above and below the liquid column are not the same, column height will be affected and flow rate readings may be unreliable.

The subject flow measurement device has certain limitations in that it will only provide an indication of flow rate over a discrete range for which it is specifically designed. Also, this device is not well suited to the measurement of sudden sharp changes in flow rate as it takes some finite time interval for the liquid column height to equilibrate with a new flow rate. However, the comparative simplicity and reliability of the subject invention more than offsets these disadvantages in many applications.

FIG. 2 depicts an embodiment of the subject device which is particularly easy to fabricate. In this embodiment the main portion of the housing 21 is a relatively large, hollow cylindrical body. A hollow tube 23 has a liquid inlet 22 at one end. This tube 23 forms the first chamber inside the main body of the housing 21. Liquid introduced into the inlet 22 passes through the tube 23 into a second chamber 25 the external walls of which are the housing 21. The lower boundary of the second chamber 25 is a solid disk 26 having two holes. The first hole is a nozzle 27 in the disk 26 through which liquid is drained from the second chamber 25 and less directly tube 23. The second hole 29 in the disk 26 is mated to an overflow tube 30. The overflow tube 30 extends vertically from the disk 26 to a region above the flow measurement zone 42. When the liquid level in the second chamber 25 rises above the overflow tube 30, excess liquid flows into the overflow inlet 33. Liquid through both the nozzle 27 and the overflow tube 30 is conveyed to a lower chamber 35 below the disk 26 and then out the outlet 40. Calibration markings in the flow measurement zone 42 relate liquid height in the second chamber 25 to liquid flow rate.

FIG. 3 depicts the solid disk 26 from FIG. 2 in cross-section. The nozzle 27 and second hole 29 in the disk 26 are clearly shown.

The vertical walls of the first and second chambers are in general conveniently essentially parallel. However, if desired, the vertical walls of the chambers can deviate from parallel.

To simplify fabrication, the first and second chambers preferably have a circular cross-section in a horizontal plane. However, other shapes are operable.

The respective sizes of the two chambers and the constricted orifice can be readily selected empirically by one of ordinary skill in the art. The same design considerations apply as in designing certain process vessels. See Considine et al, *Handbook of Applied Instrumentation*, pp. 5-57 to 5-59 (1964). The orifice size is set so that liquid leaves the flow measurement device as rapidly as it is introduced at the anticipated average flow rate when the liquid column in the flow measurement zone achieves the desired height. The orifice can be part of a nozzle or venturi.

This flow measurement device can be readily calibrated by introducing liquids at several known flow rates within the range to be measured. The height of liquid in the flow measurement zone at each predetermined flow rate provides a calibration point. Advantageously, the liquid used for calibration should be essentially identical in composition to that with which the device is to be used, since differences in viscosity can make a substantial difference in the liquid column height. Accuracy of flow rate determinations within $\pm 2\%$ has been routinely achieved following calibration.

The subject invention is particularly useful in measuring the flow through a normally partially-full pipe. If the pipe connected to the flow measurement device inlet is full of liquid, sudden changes in flow rate may interfere with accurate determination of the liquid column height. It is desirable in the device itself gravity alone provides the driving force for the liquid flow. In one preferred embodiment of the subject invention, this device is used to measure the flow rate of cell effluent from a chlor-alkali cell.

One of ordinary skill in the art will perceive a number of modifications which can be made to the subject invention without departing from the scope of this invention. For example, a transparent, vertical tube having a small diameter and connected at its lower end with the first chamber can serve as the flow measurement zone. This small diameter tube if secured as an external appendage to the main body of the housing would be more visible. The upper end of this tube is conveniently connected to a liquid outlet. A float of low mass could also be used to improve visibility of the liquid column height.

It may be desirable to make some provision for controlling flow rate, especially when the capacity of the measurement device is exceeded. Also, a means for sampling the liquid can be advantageous. All of the aforementioned modifications of the subject invention as well as others are within the ordinary skill of one in the art.

The following example illustrates but is not otherwise intended to limit this invention.

EXAMPLE 1

A flow measurement device similar to that depicted in FIG. 2 was fabricated. The numbers in parentheses correspond to those in FIG. 2. The main housing (21) was constructed from a 55-inch long Plexiglas acrylic plastic tube having a 4-inch outside diameter. All tubes and piping described herein have a 0.125-inch wall thickness unless otherwise indicated. This tube (21) was welded to a 4-inch diameter, 3.25-inch thick disk (26) of Plexiglas acrylic plastic. In this disk (26) had been fabricated a nozzle (27) which narrows from a diameter of 1.875 inches to 0.370 inch and a hole (29) sized to mate with the opening of a nominal 1-inch diameter schedule 80 pipe. To the lower portion of the disk (26) was welded a cup-shaped acrylic plastic piece 4 inches in diameter to form a lower chamber (35). This cup has a nominal two-inch diameter, schedule 80 pipe outlet (40) threaded into its base as well as a smaller tube with a valve for sampling.

Mated with the hole (29) in the disk (26) was a 53-inch long, nominal 1-inch diameter, schedule 80 acrylic pipe (30) projecting upward from the disk (26) inside the housing (21). This pipe constitutes the overflow leg (30).

Extending three inches above the main housing (21) is a 50-inch long, nominal 2-inch in diameter, schedule 80 acrylic pipe (23). This pipe (23) passes through a plate which seals the top of the housing (21), making this pipe (23) the only liquid inlet (22).

This device was calibrated using water flowing at predetermined rates in the range from about 1.9 to about 5.0 gallons per minute. Calibration markings (42) relating liquid column height to flow rate were made on the main housing. The inlet pipe (23) can optionally extend below the flow measurement zone (42).

Aqueous caustic, about 2.3 molar, was introduced into this calibrated flow measurement device. Visual inspection of the liquid column height in the main chamber relative to the calibration marks indicated a flow rate of 4.5 gallons per minute. Measurement of the flow rate by conventional techniques confirmed the accuracy of the measured value ±2 percent.

What is claimed is:

1. A device for measuring the flow of liquid through a pipe or conduit normally partially full of the liquid comprising:
   (a) a housing;
   (b) a liquid inlet into the housing communicating with the upper portion of a first, generally vertically-disposed chamber, said inlet being connected to a pipe or conduit normally partially full of liquid;
   (c) said first chamber communicating in its lower region with a constricted orifice communicating in turn wit a liquid outlet;
   (d) said first chamber also communicating with a second chamber in a region above the orifice;
   (e) said orifice and first and second chambers being sized and disposed so that the height of liquid in the second chamber is proportional to the rate of flow of the liquid through the pipe or conduit;
   (f) said second chamber having at least one generally vertical section below the point at which theliquid inlet communicates with the first chamber but above the orifice, said section constituting a flow measurement zone;
   (g) said second chamber communicating with an outlet from the housing at a point above the flow measurement zone;
   (h) a means for determining the height of the liquid in the flow measurement zone; and
   (i) a means for relating the height of liquid in the flow measurment zone to the liquid flow rate through the pipe or conduit.

2. The device as described in claim 1 wherein the flow measurement zone consists of a non-opaque section of a wall of second chamber which is externally visible and the height of the liquid is determined by visual inspection.

3. The device as described in claim 2 wherein the flow measurement zone has visible calibration markings which relate liquid column height to flow rate.

4. The device as described in claim 1 wherein the outlet communicating with the second chamber in turn communicates with the outlet communicating with the orifice.

5. The device as described in claim 1 wherein the first chamber is a tube, the second chamber is a cylinder larger in diameter than the first chamber, the first chamber penetrating the upper flat surface of the cylinder and extending a substantial portion of the length of the second chamber.

6. The device as described in claim 5 wherein the second chamber in its lower flat surface includes the constricted orifice.

7. The device as described in claim 6 wherein the first chamber extends below the flow measurement zone.

8. The device as described in claim 7 wherein the lower surface of the second chamber is penetrated by a tube which extends essentially vertically inside the second chamber to a point above the flow measurement zone and provides an outlet for liquid.

9. The device as described in claim 8 wherein the tube penetrating the bottom of the second chamber communicates with the orifice outside.the second chamber.

* * * * *